United States Patent
Kagan et al.

(10) Patent No.: US 10,195,315 B2
(45) Date of Patent: *Feb. 5, 2019

(54) SYSTEMS AND METHODS FOR SUBCUTANEOUS ADMINISTRATION OF REDUCED PRESSURE EMPLOYING RECONFIGURABLE LUMENS

(71) Applicant: KCI Licensing, Inc., San Antonio, TX (US)

(72) Inventors: Jonathan Kagan, Hopkins, MN (US); Douglas A. Cornet, Barboursville, VA (US)

(73) Assignee: KCI Licensing, Inc., San Antonio, TX (US)

( * ) Notice: Subject to any disclaimer, the term of this patent is extended or adjusted under 35 U.S.C. 154(b) by 677 days.

This patent is subject to a terminal disclaimer.

(21) Appl. No.: 14/879,990

(22) Filed: Oct. 9, 2015

(65) Prior Publication Data

US 2016/0030645 A1    Feb. 4, 2016

Related U.S. Application Data

(63) Continuation of application No. 13/292,880, filed on Nov. 9, 2011, now Pat. No. 9,180,233.

(Continued)

(51) Int. Cl.
  *A61M 1/00* (2006.01)
  *A61M 5/14* (2006.01)

(52) U.S. Cl.
  CPC ........ *A61M 1/0031* (2013.01); *A61M 1/0035* (2014.02); *A61M 1/0084* (2013.01);
  (Continued)

(58) Field of Classification Search
  CPC .. A61M 1/035; A61M 1/0084; A61M 1/0031; A61M 1/0088
  See application file for complete search history.

(56) References Cited

U.S. PATENT DOCUMENTS 1,355,846 A    10/1920 Rannells
2,547,758 A    4/1951 Kelling
(Continued)

FOREIGN PATENT DOCUMENTS

AU    550575 B2    3/1986
AU    745271 B2    3/2002
(Continued)

OTHER PUBLICATIONS

Japanese OA/Notice of Rejection dated May 31, 2016, corresponding to Japanese Application No. 2013-539905, with English translation.

(Continued)

*Primary Examiner* — Ariana Zimbouski

(57) ABSTRACT

Systems, method, and devices are disclosed that involve reconfiguring lumens or unblocking lumens relative to a blockage to maintain flow of reduced pressure to a subcutaneous tissue site. In one instance, a multi-lumen applicator includes an applicator body having a distal end and a proximal end and formed with a plurality of apertures for receiving fluid from the tissue site and for delivering reduced pressure, a first lumen fluidly coupled to the plurality of apertures, a first activation member having at least a closed position and a open position, and a second lumen fluidly coupled to the plurality of apertures but for the first activation member being in closed position. The configuration is such that when the first activation member is moved to the open position, the second lumen is fluidly coupled to the plurality of apertures. Other systems, methods, and devices are disclosed.

15 Claims, 13 Drawing Sheets

Related U.S. Application Data

(60) Provisional application No. 61/414,711, filed on Nov. 17, 2010.

(52) U.S. Cl.
CPC ... *A61M 1/0088* (2013.01); *A61M 2005/1403* (2013.01); *A61M 2205/18* (2013.01); *A61M 2205/3331* (2013.01); *A61M 2209/10* (2013.01); *A61M 2210/02* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,197,949 A * | 3/1993 | Angsupanich ............... A61B 17/320708 600/571 |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2001/0016962 A1 | 8/2001 | Moore et al. | |
| 2001/0031943 A1 * | 10/2001 | Urie ............ A61M 1/0088 604/43 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2010/0069886 A1 | 3/2010 | Wilkes | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | H03-029665 | 2/1991 |
| JP | H0584307 A | 4/1993 |
| JP | H05245209 A | 9/1993 |
| JP | H0910315 A | 1/1997 |
| JP | 2001029434 A | 2/2001 |
| JP | 2005013728 A | 1/2005 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |

(56) References Cited

FOREIGN PATENT DOCUMENTS

| WO | 96/05873 A1 | 2/1996 |
|---|---|---|
| WO | 97/18007 A1 | 5/1997 |
| WO | 99/13793 A1 | 3/1999 |
| WO | 2010080667 A1 | 7/2010 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Wong Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

SYSTEMS AND METHODS FOR SUBCUTANEOUS ADMINISTRATION OF REDUCED PRESSURE EMPLOYING RECONFIGURABLE LUMENS

RELATED APPLICATION

This application is a continuation of U.S. patent application Ser. No. 13/292,880, entitled "Systems and Methods for Subcutaneous Administration of Reduced Pressure Employing Reconfigurable Lumens," filed Nov. 9, 2011, which claims the benefit, under 35 USC § 119(e), of the filing of U.S. Provisional Patent Application No. 61/414,711, entitled "Systems and Methods for Subcutaneous Administration of Reduced Pressure Employing Reconfigurable Lumens," filed Nov. 17, 2010. Each of the applications set forth above are incorporated herein by reference for all purposes.

FIELD

The present disclosure relates generally to medical treatment systems and, more particularly, but not by way of limitation, to systems, methods, and devices for the subcutaneous administration of reduced pressure that include reconfigurable lumens.

BACKGROUND

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, when applied to open wounds, reduced pressure is applied to tissue through a porous pad or other manifold device. The porous pad contains cells or pores that are capable of distributing reduced pressure to the tissue and channeling fluids that are drawn from the tissue. When applied subcutaneously, often the reduced pressure is delivered through a manifold that includes channels and openings in a reduced-pressure delivery apparatus.

SUMMARY

According to an illustrative embodiment, a system for providing reduced pressure to a subcutaneous tissue site and removing fluids from the subcutaneous tissue site is provided that includes a multi-lumen applicator for distributing reduced pressure at the subcutaneous tissue site, a reduced-pressure delivery conduit fluidly coupled to the multi-lumen applicator, a reduced-pressure source coupled to the reduced-pressure delivery conduit, and a purging unit fluidly coupled to the reduced-pressure delivery conduit. The multi-lumen applicator includes an applicator body formed with a plurality of apertures, a first lumen initially fluidly configured to receive liquids from the tissue site through the plurality of apertures, a second lumen initially configured to provide a purging fluid to the first lumen, and a first frangible member disposed between the first lumen and second lumen. The first frangible member is configured to rupture when exposed to a pressure greater than a first threshold pressure differential whereby at least a portion of the second lumen and a portion of the first lumen become fluidly coupled.

According to another illustrative embodiment, a system for providing reduced pressure to a subcutaneous tissue site includes a multi-lumen applicator for distributing reduced pressure at the subcutaneous tissue site, a reduced-pressure delivery conduit fluidly coupled to the multi-lumen applicator, a reduced-pressure source coupled to the reduced-pressure delivery conduit, and a purging unit fluidly coupled to the reduced-pressure delivery conduit. The multi-lumen applicator includes an applicator body formed with a plurality of apertures, a first lumen initially fluidly configured to receive liquids from the tissue site through the plurality of apertures, a second lumen initially configured to provide a purging fluid to the first lumen, and an activation member disposed between the first lumen and second lumen. The activation member is configured to fluidly couple, when activated, at least a portion of the second lumen and a portion of the first lumen whereby at least a portion of the second lumen transports the liquids from the tissue site over at least a portion of the second lumen.

According to another illustrative embodiment, a method for providing reduced pressure to a subcutaneous tissue site includes providing multi-lumen applicator for distributing reduced pressure at the subcutaneous tissue site. The multi-lumen applicator includes an applicator body formed with a plurality of apertures and at least a first lumen and a second lumen, and at least one frangible member. The method further includes disposing the multi-lumen applicator proximate to the subcutaneous tissue site, removing fluids from the subcutaneous tissue site through the first lumen, rupturing the at least one frangible member to reconfigure functionality of at least a portion the second lumen, and removing fluids from the subcutaneous tissue site at least partially through the second lumen after rupturing the at least one frangible member.

According to another illustrative embodiment, a multi-lumen applicator for delivering reduced pressure to a tissue site and receiving liquids includes an applicator body having a distal end and a proximal end and formed with a plurality of apertures for receiving liquid from the tissue site and for delivering reduced pressure, a first lumen fluidly coupled to the plurality of apertures, a first activation member having at least a closed position and an open position, and a second lumen fluidly coupled to the plurality of apertures when the first activation member is in the open position but not when in the closed position. The configuration is such that when the first activation member is moved to the open position, the second lumen is fluidly coupled to the plurality of apertures.

According to another illustrative embodiment, a method for providing reduced pressure to a subcutaneous tissue site includes providing a multi-lumen applicator for distributing reduced pressure at the subcutaneous tissue site. The multi-lumen applicator includes an applicator body formed with a plurality of apertures, a purge lumen, a first lumen fluidly coupled to the plurality of apertures and to the purge lumen, an activation member operable to move from a closed position to an open position when activated, and a second lumen fluidly coupled to the purge lumen when the activation member is in the open position. The method further includes disposing the multi-lumen applicator proximate to the subcutaneous tissue site, removing fluids from the subcutaneous tissue site through the first lumen, activating the activation member of the multi-lumen applicator such that the second lumen is fluidly coupled to the purge lumen, and removing fluids from the subcutaneous tissue site at least partially through the second lumen after activating the activation member.

According to another illustrative embodiment, a multi-lumen applicator for delivering reduced pressure to a tissue site and receiving liquids includes an applicator body having a distal end and a proximal end and formed with a first plurality of apertures and a second plurality of apertures for receiving liquid from the tissue site and for delivering reduced pressure, a first lumen fluidly coupled to the first plurality of apertures, a second lumen fluid coupled to the second plurality of apertures, and a first plurality of activation members coupled over the second plurality of apertures. The first plurality of activation members are operable to move from a closed position to an open position when activated.

According to another illustrative embodiment, a multi-lumen applicator for delivering reduced pressure to a subcutaneous tissue site includes an applicator body having a proximal end and a distal end and formed with plurality of apertures for distributing reduced pressure, a first lumen fluidly coupled to the plurality of apertures, a second lumen fluidly coupled to the plurality of apertures, and a removal filament member disposed within the second lumen and operable to be removed when fluid flow in the second lumen is desired.

According to another illustrative embodiment, a system for delivering reduced pressure to a subcutaneous tissue site includes a connector and a multi-lumen applicator. The multi-lumen applicator includes an applicator body having a proximal end and a distal end and formed with plurality of apertures for distributing reduced pressure, a first lumen fluidly coupled to at least a portion of the plurality of apertures and to the connector, and a second lumen fluidly coupled to at least a portion of the plurality of apertures and to the connector. The system further includes a reduced-pressure source fluidly coupled to the connector, a purge unit fluidly coupled to the connector, and a controller coupled to the connector. The controller is operable to initially couple the first lumen to the reduced-pressure source to provide reduced pressure thereby to at least a portion of the plurality of apertures, initially fluidly couple the second lumen to the purge unit, and when the first lumen becomes occluded, couple the first lumen to the purge unit and the second lumen to the reduced-pressure source.

According to another illustrative embodiment, a method for delivering reduced pressure to a subcutaneous tissue site includes providing a multi-lumen applicator for distributing reduced pressure at the subcutaneous tissue site. The multi-lumen applicator includes an applicator body formed with a plurality of apertures, a first lumen fluidly coupled to at least a portion of the plurality of apertures, and a second lumen fluidly coupled to at least a portion of the plurality of apertures. The method further includes coupling the first lumen to a reduced-pressure source, coupling the second lumen to a purge unit, disposing the multi-lumen applicator proximate to the subcutaneous tissue site, removing fluids from the subcutaneous tissue site through the first lumen, and when the first lumen becomes substantially blocked, coupling the second lumen to the reduced-pressure source and the first lumen to the purge unit.

According to another illustrative embodiment, a system for delivering reduced pressure to a subcutaneous tissue site includes a multi-lumen applicator comprising. The multi-lumen applicator includes an applicator body having a proximal end and a distal end and formed with plurality of apertures for distributing reduced pressure, a first lumen fluidly coupled to at least a portion of the plurality of apertures, and a second lumen fluidly coupled to at least a portion of the plurality of apertures. The system further includes a reduced-pressure source fluidly coupled to the first lumen, and a blockage-removal device initially disposed within the first lumen. The blockage-removal device is operable to remove a blockage from within the first lumen when the blockage-removal device is activated.

Other aspects, features and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Providing reduced pressure to a subcutaneous tissue site may assist with removing fluids, e.g., ascites or exudates, or enhance tissue growth as an aspect of reduced pressure therapy. As used throughout this document, "or" does not require mutual exclusivity. In applying reduced pressure to a subcutaneous tissue site often a multi-lumen applicator is used. At times, blockage of lumens may occur and pose a problem to the ongoing treatment. According to an illustrative embodiment, the lumens may be reconfigured relative to the blockage in order to restore flow of reduced pressure to the subcutaneous tissue site or to remove the blockage. In other illustrative embodiments, the blockage may be removed using a blockage-removal device.

Figure 1:
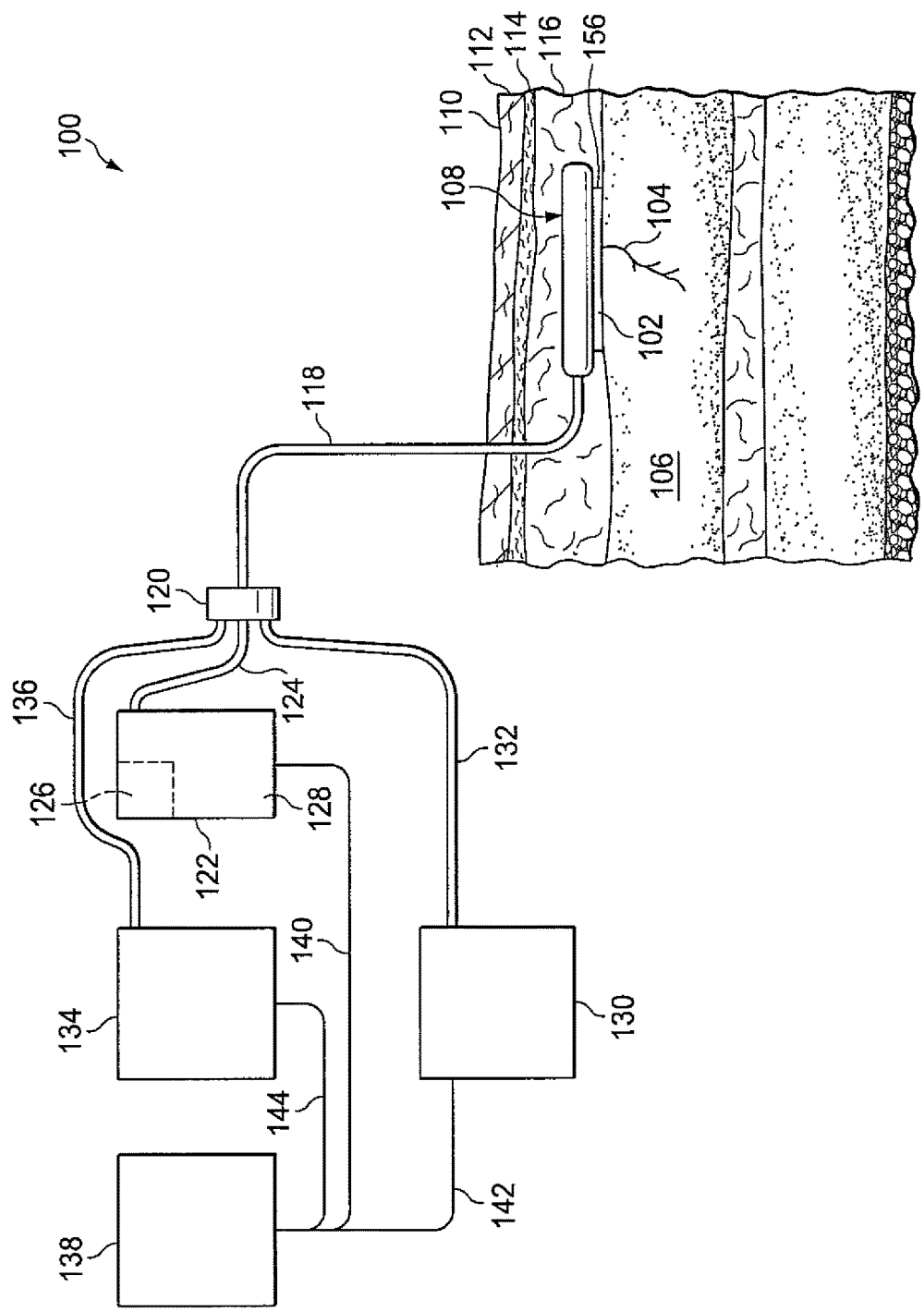
FIG. 1 is a schematic diagram, with a portion shown in cross section, of an illustrative embodiment of a system for providing reduced pressure to a subcutaneous tissue site and for removing fluids from the subcutaneous tissue site.

Referring now to the drawings and initially to FIG. 1, an illustrative embodiment of a system 100 for providing reduced pressure to a subcutaneous tissue site 102 is presented. The subcutaneous tissue site 102 may be, for example, a defect 104 in or on a bone 106 (e.g., a fractured bone). The subcutaneous tissue site 102 may be any site that may benefit from treatment with reduced pressure to remove fluids or as an aspect of reduced pressure therapy. The subcutaneous tissue site 102 may be the bodily tissue of any human, animal, or other organism, including bone tissue, adipose tissue, muscle tissue, vascular tissue, connective tissue, cartilage, tendons, ligaments, or any other tissue.

The system 100 includes a multi-lumen applicator 108 that is inserted into the patient 110 and placed proximate to the subcutaneous tissue site 102. In the illustrative non-limiting embodiment, the multi-lumen applicator 108 is shown having been inserted through epidermis 112, dermis 114, and into subcutaneous tissue 116. The multi-lumen applicator 108 is positioned proximate to the subcutaneous tissue site 102.

The multi-lumen applicator 108 is fluidly coupled to a reduced-pressure delivery conduit 118, which may be a multi-lumen conduit that has lumens coordinated and fluidly coupled to the multiple lumens of the multi-lumen applicator 108. The reduced-pressure delivery conduit 118 may be fluidly coupled to a connector 120 that may facilitate connecting multiple lumens to the multiple lumens of the reduced-pressure delivery conduit 118.

A reduced-pressure source 122 is fluidly coupled by a conduit 124 to the connector 120 to provide reduced pressure thereto. The reduced-pressure source 122 may include a reduced-pressure supply portion 126 and a fluid reservoir 128. The reduced-pressure supply portion 126 may be a vacuum pump, wall suction, or any other source of reduced pressure. The fluid reservoir 128 may provide a place to receive and retain fluids delivered from the patient 110.

Reduced pressure is typically a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, quantitative values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure. For example, going from −50 mm Hg to −100 mm Hg may be referred to as an increase in reduced pressure, but on an absolute pressure scale it is a decrease in pressure.

A purging unit 130 may be fluidly coupled by a conduit 132 to the connector 120. The purging unit 130 may provide atmospheric air or another purging gas or pressurized gas to the multi-lumen applicator 108 in order to avoid or remove blockages therein. The purge gas provided by the purging unit 130 may be at an elevated pressure with respect to atmosphere or relative to the operational pressure of the system 100.

A liquid source 134 may be fluidly coupled by a conduit 136 to the connector 120. The liquid source 134 may be used to provide a liquid purge to the multi-lumen applicator 108 or may be used to provide a treatment liquid, or therapeutic liquid, to the multi-lumen applicator 108 and ultimately to the subcutaneous tissue site 102.

A controller 138 may be coupled by coupling lines 140, 142 and 144 to the reduced-pressure source 122, purging unit 130, and liquid source 134, respectively. The controller 138 may include a microprocessor, memory, and other components for providing control to the reduced-pressure source 122, purging unit 130, and liquid supply 134. The controller 138 may also be coupled to the connector 120 to control valves within the connector 120 as shown in the illustrative embodiment of FIG. 11.

Figure 2:
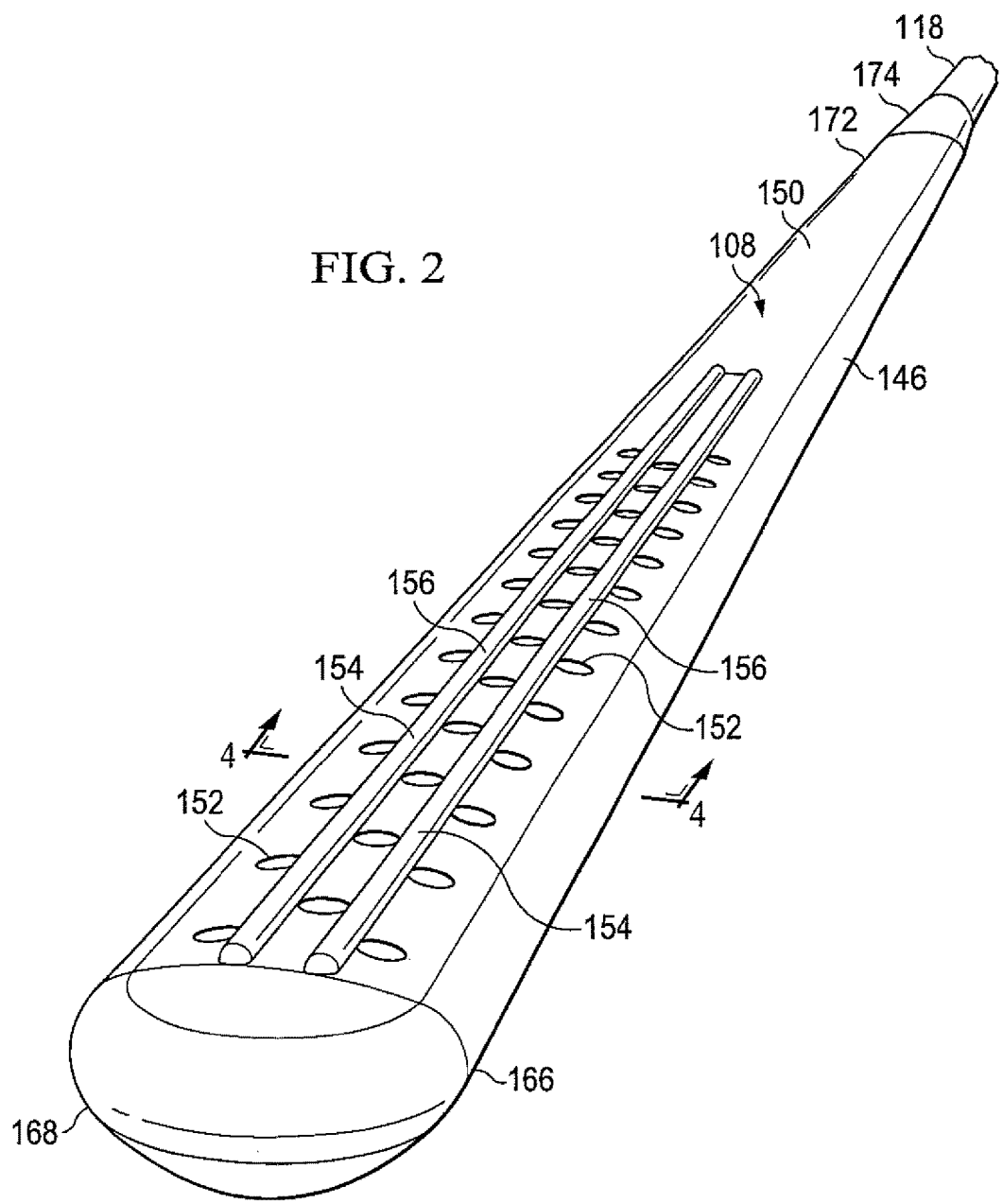
FIG. 2 is a schematic, perspective view of an illustrative embodiment of a multi-lumen applicator.
Figure 3:
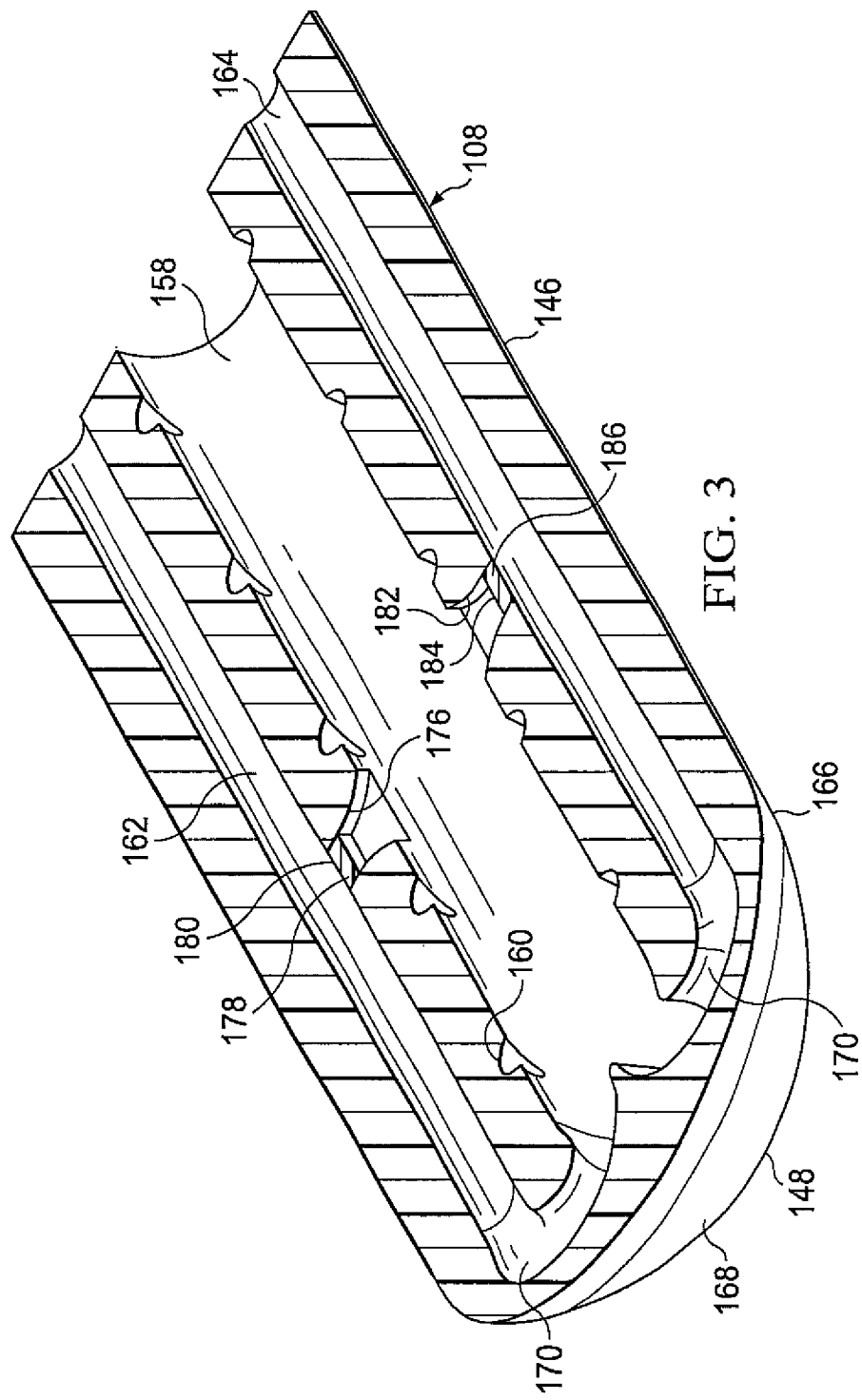
FIG. 3 is a longitudinal cross section of the multi-lumen applicator of FIG. 2 showing a distal end.
Figure 4:
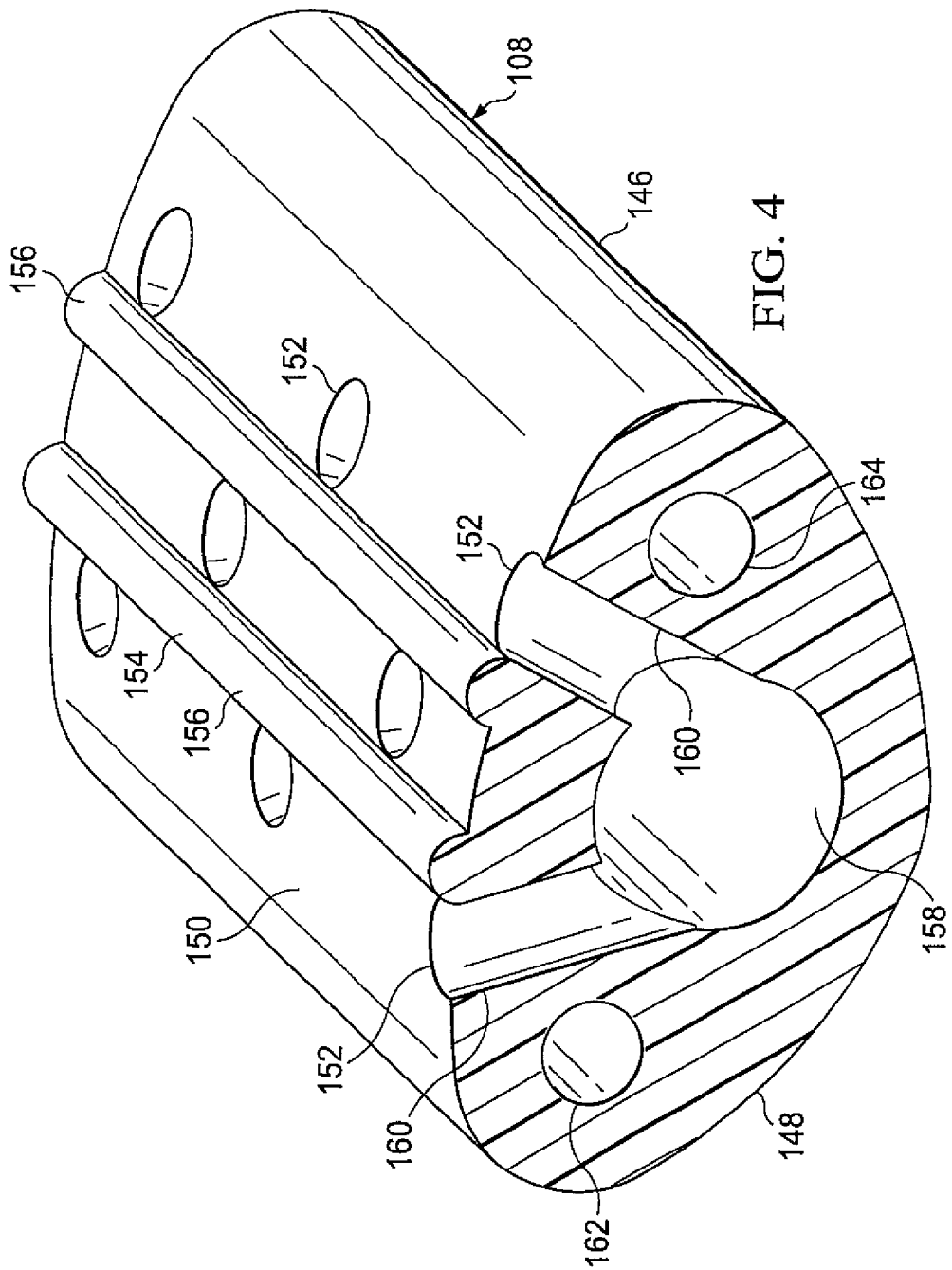
FIG. 4 is a lateral cross section of the multi-lumen applicator of FIG. 2 taken along line 4-4.

Referring now primarily to FIGS. 2-4, an illustrative embodiment of a multi-lumen applicator 108 is presented. The multi-lumen applicator 108, or manifold, is formed with an applicator body 146, which has a first side 148 and a second, tissue-facing side 150. The multi-lumen applicator 108 may be formed by injection molding or other techniques. The multi-lumen applicator 108 may also be extruded into parts and then bonded or otherwise coupled to form an integral unit. Alternatively, the multi-lumen applicator 108 may be extruded and then undergo a secondary controlled melt "tipping" process to form an integral unit. The multi-lumen applicator 108 may be made from a flexible or semi-rigid material. For example, the multi-lumen applicator 108 may be made from any medical-grade polymer, such as polyurethane. In one embodiment, the multi-lumen applicator 108 is made from a material with a stiffness of approximately 80 Shore A, but other stiffnesses may be used. A coating may be added to the multi-lumen applicator 108 to avoid material buildup on the multi-lumen applicator 108.

A plurality of apertures 152 are formed on the second, tissue-facing side 150 of the applicator body 146 for providing reduced pressure to the subcutaneous tissue site 102. While the apertures 152 are shown in a symmetrically spaced pattern, it should be understood that the apertures 152 may be formed with any pattern or with a random placement. A plurality of manifold surface features 154 may be formed on the second, tissue-facing side 150. The plurality of manifold surface features 154 may include a plurality of standoffs or offsets 156. The plurality of offsets 156 may be formed integrally with or coupled to the second, tissue-facing side 150 of the applicator body 146. The offsets 156 may be any surface feature creating effective flow channels between the second, tissue-facing side 150 and the tissue site. The manifold surface features 154 may detach from the applicator body 146 when the multi-lumen applicator 108 is percutaneously removed, and the manifold surface features 154 may be bioresorbable.

The plurality of apertures 152 are fluidly coupled to the first lumen 158 that is formed in the applicator body 146. The first lumen 158 may be fluidly coupled to the apertures 152 by a plurality of conduits 160. The first lumen 158 extends the longitudinal length of the applicator body 146. The first lumen 158 may initially be used as an evacuation lumen to deliver reduced pressure to the plurality of apertures 152 and to receive and transport fluids from the subcutaneous tissue site 102.

The applicator body 146 is also formed with a second lumen 162 and may have a third lumen 164 or even more lumens. The second lumen 162 and third lumen 164 also extend the longitudinal length of the applicator body 146. The second lumen 162 and third lumen 164 may initially be used as purge lumens, or vent lumens. While this illustrative embodiment shows two purge lumens, it should be understood that any number of purge lumens may be used. Additionally, the second lumen 162 and third lumen 164 are shown symmetrically spaced about the first lumen 158, and while the symmetric orientation may enhance performance, other orientations may be used. Additional lumens, such as a pressure sensing lumen (not explicitly shown), may be included within the applicator body 146. The purge lumens may also serve as pressure sensing lumens. It should be noted that although a slightly elliptical or triangular shape is presented, the cross sectional shape of the applicator body 146 may be any of those previously mentioned or even irregular or other shapes.

On the distal end 166 of the applicator body 146, an end cap 168 is formed or coupled. The end cap 168 is formed with a header space 170 that allows the second lumen 162 and the third lumen 164 (and any additional lumens) to be fluidly coupled to the first lumen 158. The end cap 168 is formed integrally to or as part of the applicator body 146 and, thus, avoids the risk of the end cap 168 becoming dislodged during removal from the patient 110. At a proximal end 172 (FIG. 2) of the applicator body 146, a connecting element, or connector 174, may be coupled to provide easy connection with the reduced-pressure delivery conduit 118, which in turn is fluidly coupled to the reduced-pressure source 122 and also to the purging unit 130 or liquid source 134.

Referring now to FIGS. 2-5C, the multi-lumen applicator 108 has provisions to reconfigure lumens, e.g., the first lumen 158, second lumen 162, and third lumen 164, in order to restore flow through the apertures 152. In this illustrative embodiment, a first port 176 is formed between the first lumen 158 and the second lumen 162. Port typically refers to an open flow path either between two lumens or a lumen and an exterior of the multi-lumen applicator 108. The first port 176 fluidly couples the first lumen 158 and the second lumen 162 when a first activation member 178 is in an open, or activated, position. The first activation member 178 may be any member that provides a closed position in one state and an open position in another state that allows flow. For example, the first activation member 180 may be a first frangible member 180 as shown in FIG. 3 in the closed position. The term "frangible" is used generally to indicate a material that fails, ruptures, tears, or dissolves in a predictable manner. The frangible material fails, ruptures, tears, or dissolves in a repeatable manner between devices.

The first frangible member 180 (and other frangible members) may be a frangible disc or frangible port cover, which may be a piece of material covering a port that is designed to rupture or open at a first threshold pressure differential or to dissolve and thereby open after being exposed to a liquid for at least a threshold time. In the embodiment where the activation member 178 dissolves in the presence of a liquid (body fluids or a supplied liquid), the activation member 178 may be formed from a polylactic acid (PLA), polyglycolic acid (PGA), polyactic co-glycolic acid (PLGA), hydrogel, or cross-linked or hardened gelatine, or other suitable material. In other embodiments, the first activation member 178 may be a valve with a remote attachment, e.g., a line, that can be pulled to open the first activation member 178. In another illustrative embodiment, the first activation member 178 may be a plug in a port that under pressure is released from the port and is removed.

A second port 182 is formed between the first lumen 158 and the third lumen 164. The second port 182 fluidly couples the first lumen 158 and the third lumen 164 when a second activation member 184 is in an open position. The second activation member 184 may be a second frangible member 186 or other device analogous to those mentioned for first activation member 180.

In operation, the multi-lumen applicator 108 may be inserted surgically or using minimally invasive surgery into the patient. Typically, the multi-lumen applicator 108 is removed percutaneously after use or in one embodiment may be bio-absorbable and left in place to absorb. In one illustrative embodiment in which it is desirable to provide reduced-pressure treatment with the multi-lumen applicator 108 for an extended period of time, e.g., 24 hours, the multi-lumen applicator 108 addresses blocks or the possibility of blocks by reconfiguring lumens during use. Thus, after the multi-lumen applicator 108 is inserted, and reduced pressure is supplied to the subcutaneous tissue site 102, flow may continue for a first period of time. After this first period of time, which may be a preset time or may be when a blockage occurs, the first activation member 178 may be activated to open a flow path that reconfigures flow by reconfiguring the lumens 158, 162, or 164. The reconfiguration increases the likelihood that the system 100 will continue to operate with flow for the desired time duration. A number of illustrative, non-limiting examples of how lumens may be reconfigured or how blockages may be removed will be presented.

Figure 5A:
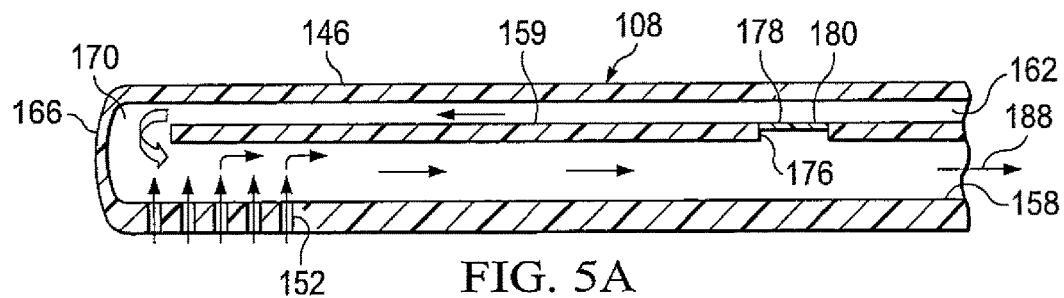
FIGS. 5A-5C are schematic cross sections of an illustrative embodiment of a multi-lumen applicator that includes a first activation member shown in different states.
Figure 5B:
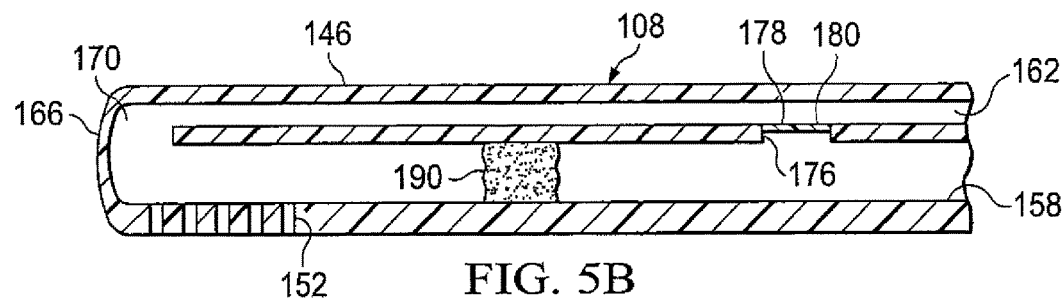
Figure 5C:
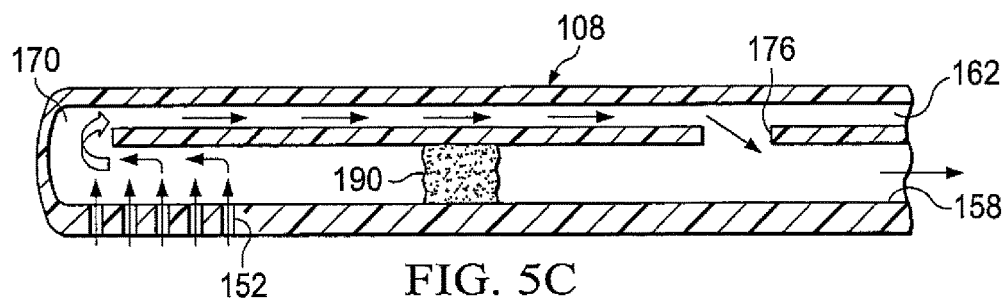

Referring now primarily to FIGS. 5A-5C, an illustrative embodiment of a multi-lumen applicator 108 is presented to show how lumens, e.g., lumens 158 and 162, may be reconfigured according to one illustrative embodiment. For purposes of illustration, the multi-lumen applicator 108 is shown with only two lumens: a first lumen 158 and a second lumen 162. It should be understood that other lumens or additional lumens may be involved.

The multi-lumen applicator 108 in FIG. 5A shows an initial state in which reduced pressure is delivered to the first lumen 158 thereby causing a flow 188 of fluid in an ante grade direction. The first lumen 158 in this initial condition serves as an evacuation lumen. The multi-lumen applicator 108 also includes the second lumen 162 that initially serves as a purge lumen providing a purge fluid, such as air, to the first lumen 158 to inhibit blocking or eliminate blocking. The purge fluid may be provided on a periodic basis. It should be appreciated that the second lumen 162 provides a purging fluid that travels through a head space 170 at a distal end 166 to avoid blockages. In this initial state, reduced pressure is distributed to a plurality of apertures 152 in an applicator body 146. Fluid, e.g., wound effluent, is pulled from the tissue site (not shown), e.g., the subcutaneous tissue site 102 in FIG. 1, into the apertures 152 and along the first lumen 158 to a fluid reservoir (not shown), e.g., the fluid reservoir 128 in FIG. 1. Normal operation may involve, for example, and not by way of limitation, a reduced pressure in the range of −100 mm Hg (−13.3 kPa) to −200 mm Hg (−26.6 kPa).

A first port 176 may be formed as an aspect of a wall 159 between the first lumen 158 and second lumen 162. The first port 176 is controlled by a first activation member 178 that has a closed position as shown in FIGS. 5A-B and an open position as shown in FIG. 5C. The first activation member 178 assumes the open position when activated. The first activation member 178 may be, for example, a first frangible member 180.

Referring now primarily to FIG. 5B, after sufficient time, a blockage 190 may result within the first lumen 158. The blockage 190 may inhibit or completely stop flow within the first lumen 158 and thereby inhibit or stop flow of fluids from the tissue site through the apertures 152. When a controller or detection device or an operator determines that a blockage, e.g., the blockage 190, has occurred, an increased pressure, e.g., −300 mm Hg (−39.9 kPa) or −350 mm Hg (−46.6 kPa) may be applied to activate the first activation member 178 and in this embodiment to rupture the first frangible member 180. After the first activation member 178 is activated, the lumens are reconfigured with respect to flow in portions and flow may begin to occur as shown in FIG. 5C. The first activation member 178 may also be activated by exposure to liquid or by removal of a remote line (not shown) that activates a valve or opens the activation member 178.

Referring to FIGS. 5A-5C and primarily to FIG. 5C, the first activation member 178, which in this embodiment is a first frangible member 180, has been activated such that the first port 176 is in an open position. Thus, as reduced pressure is applied to the first lumen 158, fluid flows through the aperture 152 from the tissue site, traverses the head space 170, and flows through a portion of the second lumen 162, through the first port 176 as shown, and then continues through the first lumen 158 where flow may be received by a fluid reservoir, such as the fluid reservoir 128 in FIG. 1. Thus, the reconfiguring of at least a portion of the first lumen 158 and second lumen 162 allows flow to continue notwithstanding the blockage 190.

Figure 6:
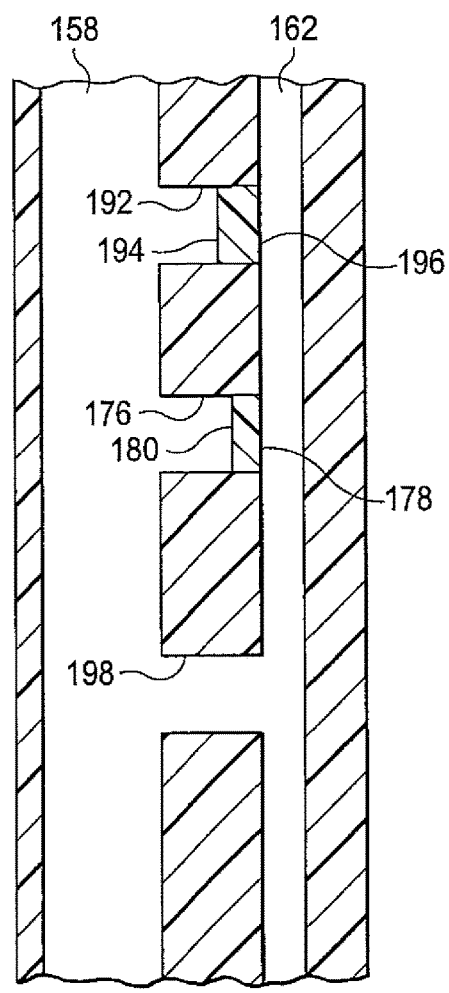
FIG. 6 is a schematic longitudinal cross section of two lumens that may be included in an illustrative embodiment of a multi-lumen applicator.

While only one port 176 with a first activation member 178 is shown in FIGS. 5A-5C, it should be understood that multiple ports and activation members may be provided along the length of the multi-lumen applicator 108. For example, as shown in FIG. 6, a first port 176 is covered by a first activation member 178, such as a first frangible member 180 and a second port 192 is shown with a second activation member 194. The first frangible member 180 is disposed between the first lumen 158 and the second lumen 162. The first frangible member 180 is configured to rupture when exposed to a pressure greater than the first threshold pressure differential, whereby at least a portion of the second lumen 162 and a portion of the first lumen 158 are fluidly coupled. In addition, the second port 192 is shown with the activation member 194, such as an additional frangible member 196. Still another port 198 is shown in an open position.

In operation of the illustrative embodiment of FIG. 6, an initial flow is established through the port 198 until a blockage occurs, and then a first threshold pressure differential, e.g., −300 mm Hg, is used on the first activation member 178 to move the first activation member 178 to an open position. Activating the first activation member 178 causes flow to go through the first port 176. Later, if another blockage occurs, a second threshold pressure differential, e.g., −350 mm Hg, may be used to activate the additional activation member 196 and thereby open the additional port 192 to provide another reconfigured flow path through the lumens. As before, the activation of the activation members 178 and 196 may also be initiated based on elapsed time.

Figure 7:
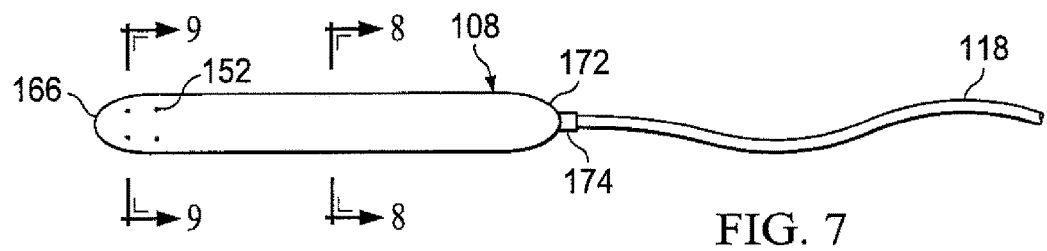
FIG. 7 is a schematic, plan view of an illustrative embodiment of a multi-lumen applicator for use as part of a system for providing reduced pressure to subcutaneous tissue site and for removing fluids from the subcutaneous tissue site.
Figure 8:
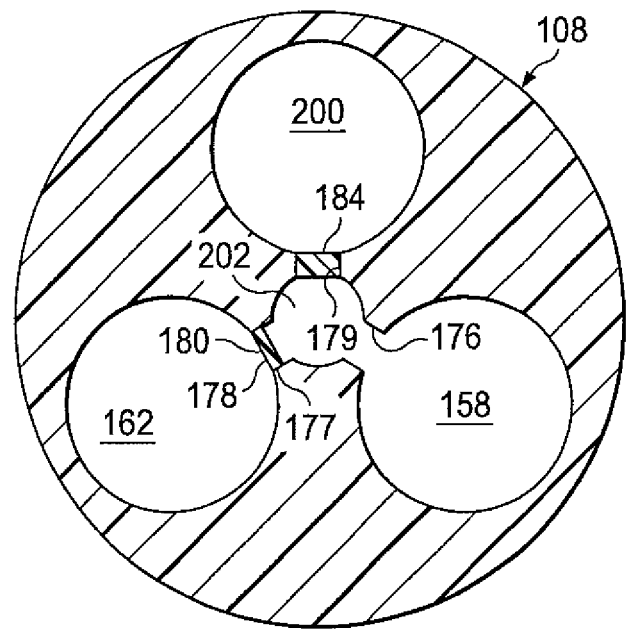
FIG. 8 is a schematic lateral cross section taken along line 8-8 of the multi-lumen applicator of FIG. 7.

Referring now primarily to FIGS. 7-8, another illustrative embodiment of a multi-lumen applicator 108 is presented. The multi-lumen applicator 108 has a distal end 166 and a proximal end 172. A plurality of apertures 152 may be formed near the distal end 166 for providing reduced pressure to a tissue site, e.g., subcutaneous tissue site 102 in FIG. 1. A connector 174 may be used to connect a reduced-pressure delivery conduit 118 to the multi-lumen applicator 108. In one illustrative embodiment, three lumens, which are shown in cross section in FIG. 8, e.g., a first lumen 158, a second lumen 162, and a third lumen 200, may be placed around a fourth lumen 202. In this illustrative embodiment, in the initial state, only the first lumen 158 is active, or open, for removing fluids from the tissue site and is in fluid communication with the fourth lumen 202. The fourth lumen 202 is initially a purging lumen.

The first lumen 158 has a first port 176, which is discrete, that fluidly couples the first lumen to the fourth lumen 202. The second lumen 162 has a second port 177, which is discrete, that fluidly couples the second lumen to the fourth lumen 202. The third lumen 200 has a third port 179, which is discrete, that fluidly couples the third lumen 200 to the fourth lumen 202. In this illustrative embodiment, the first port 176 is initially in an open position. The second port 177 is initially closed by a first activation member 178, e.g., a first frangible member 180. The third port 179 is initially closed by a second activation member 184, e.g., a second frangible member.

After a specified period of time or when it is determined that a blockage exists, a pressure is applied to the lumens 158, 162, 200 that creates a pressure differential that surpasses a first threshold pressure differential whereby the first activation member 178 may be activated. Alternately, this activating pressure can be applied to lumen 202 to create an activation pressure differential. For example, if the first activation member 178 is the first frangible member 180, the first frangible member 180 may be subjected to a pressure differential greater than the first threshold pressure differential, e.g., −300 mm Hg, such that the first frangible member 180 ruptures. The ruptured first frangible member 180 provides fluid communication between the second lumen 162 and the fourth lumen 202. At this point, fluids from the tissue site flow from the apertures 152 through the second lumen 162 while the fourth lumen 202 acts as a purging lumen.

When sufficient time has passed or when a blockage exists in the second lumen 162, the second activation member 184 may be activated to allow fluid communication between the third lumen 200 and the fourth lumen 202. In this way, additional flow may go from the apertures 152 through the third lumen 200 to a fluid reservoir. The use of the activation members 178, 184 in FIG. 8 may simplify the connector and reduce-pressure source design since the inactive lumens (e.g., initially lumens 162, 200) can be exposed to the reduced pressure.

Figure 9:
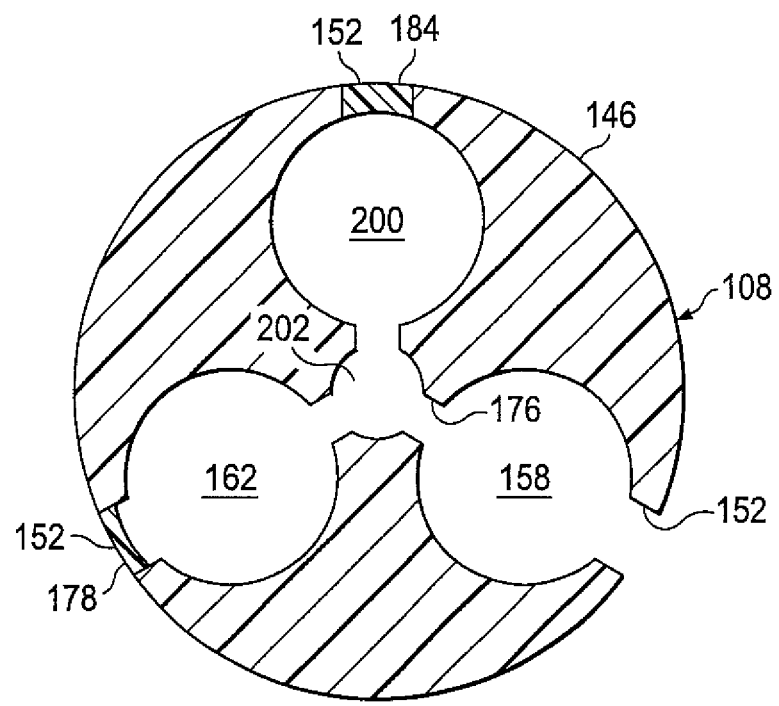
FIG. 9 is a schematic, lateral cross section taken along line 9-9 in FIG. 7 of the illustrative, non-limiting multi-lumen applicator.

Referring now primarily to FIG. 9, another illustrative embodiment of a portion of a multi-lumen applicator 108 is presented. The multi-lumen applicator 108 of FIG. 9 is analogous in most respects to the multi-lumen applicator 108 of FIG. 7, and accordingly, some parts are labeled the same but not further described here. It should be noted, however, that while the section line 9-9 is shown in FIG. 7, this embodiment is nonetheless distinct from that described above in connection with FIGS. 7 and 8 in a number of respects. In this embodiment, the multi-lumen applicator 108 is formed with an applicator body 146 having a first lumen 158, second lumen 162, third lumen 200, and a fourth lumen 202. The lumens 158, 162, 200 are positioned around the fourth lumen 202 and each lumen has at least one aperture or port of a plurality of apertures 152 that provides access to an exterior of the multi-lumen applicator 108. For example, in this illustrative embodiment, a first port 176 is formed between the first lumen 158 and the fourth lumen 202. In this instance, in the initial state, fluids are drawn through the portion of apertures 152 associated with the first lumen 158 until a blockage occurs. Then pressure, i.e., the pressure differential, may be increased to activate a first activation member 178 or plurality of first activation members that cover a portion of apertures 152 associated with the second lumen 162. Thus, the second lumen 162 begins to serve as an evacuation lumen for liquids from the tissue site.

When the second lumen 162 becomes blocked, the pressure may be increased to activate a second activation member 184 or plurality of first activation members that cover a portion of apertures 152 associated with the third lumen 200. Thus, the third lumen 200 begins to serve as an evacuation lumen for liquids from the tissue site. The fourth lumen 202 serves as a purge lumen for each of the lumens 158, 162, 200.

Throughout this document, activation members are referenced and typically discussed in the context of frangible members. It should be understood that the activation members may be activated by pressure exceeding a threshold pressure differential or by mere passage of time with the activation members exposed to a fluid. Thus, for example, after a first threshold time period, the first activation member may dissolve to the point that the first activation member ruptures or otherwise allows fluid flow. In another illustrative embodiment, the activation members may be activated by pulling a line that removes a plug or opens a valve, or any other technique to open the port in situ.

As previously noted, the activation members, e.g., activation members 178 and 184, may be frangible members in some embodiments. The frangible members may be controlled with respect to when they open or rupture by controlling a number of variables. For example, the material of the frangible member may be thin, strong, or stretchy, consistent, or scored to create a location for the failure. In addition, rupture of the frangible members may be controlled by thickness of various portions and may have an adhesive for controlling aspects of the frangible members.

Figure 10:
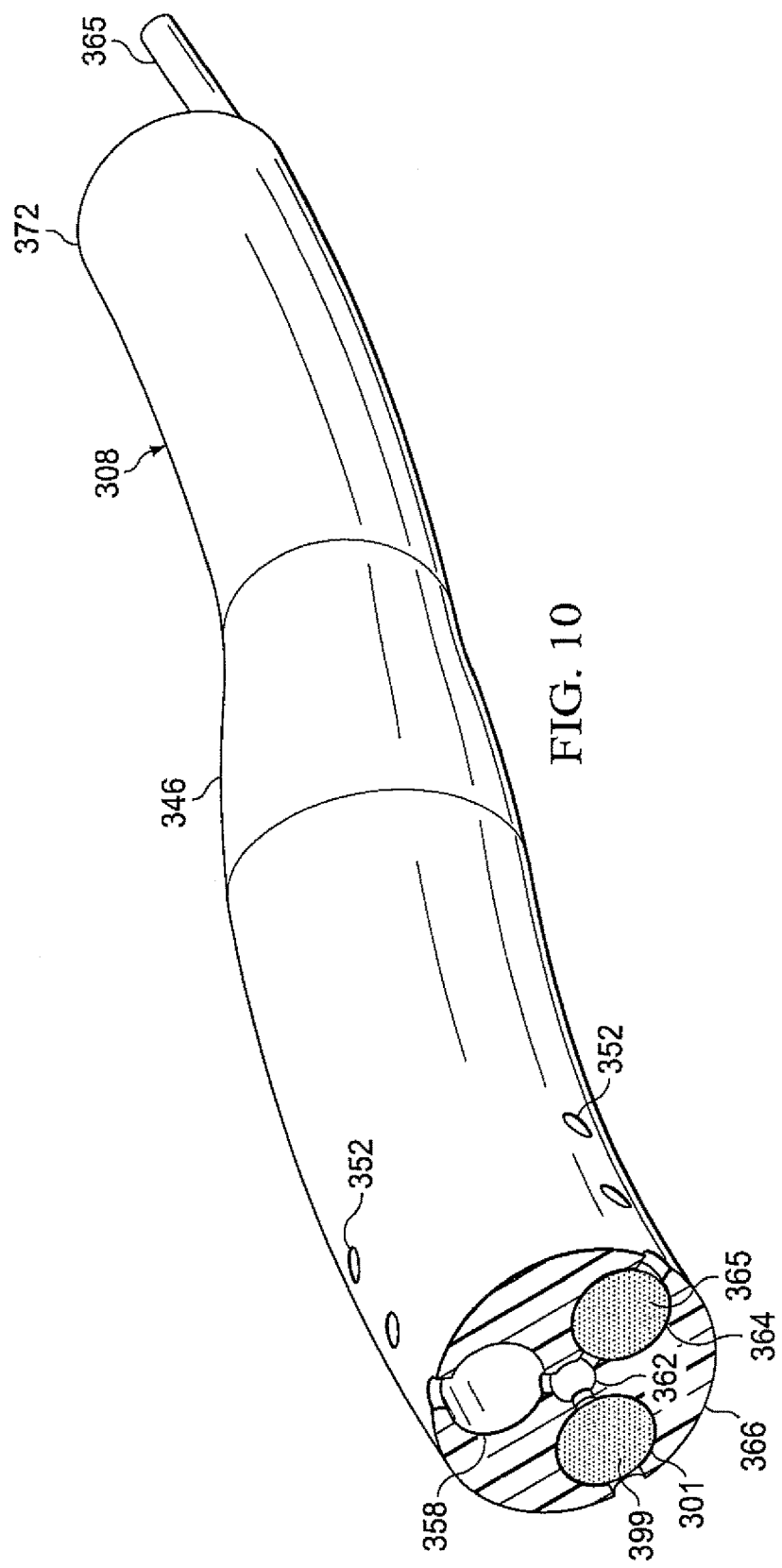
FIG. 10 is a schematic, perspective view (with a portion shown in cross section) of another illustrative embodiment of a multi-lumen applicator for distributing reduced pressure that may be used as an aspect of a system for providing reduced pressure to a subcutaneous tissue site and for removing fluids from the subcutaneous tissue site.

Referring now primarily to FIG. 10, another illustrative embodiment of a portion of a multi-lumen applicator 308 is presented. The multi-lumen applicator 308 includes an applicator body 346 formed with a plurality of apertures 352. The multi-lumen applicator 308 includes a first lumen 358, a second lumen 362, a third lumen 364, and a fourth lumen 301. The multi-lumen applicator 308 is shown in the initial state in which the first lumen 358 serves as an evacuation lumen and the second lumen 362 serves as a vent or purge lumen. Thus, fluids from the tissue site are drawn through at least a portion of the plurality of apertures 352, into the first lumen 358, and moved from the distal end 366 to the proximal end 372 where the fluids are delivered into a fluid reservoir.

The third lumen 364 and fourth lumen 301 are initially filled by filaments 365, 399. Thus, the third lumen 364 is initially filled by the first filament 365, and the fourth lumen 301 is filled by a second filament 399. Each filament 365, 399 may be a nylon monofilament or wire that substantially fills the space of the noted lumens to prevent flow therein.

In operation, the first lumen 358 is initially used to deliver reduced pressure and remove fluids through at least a portion of the apertures 352. When the first lumen 358 is blocked or sufficient time has passed, the first filament 365 may be removed from the third lumen by pulling the first filament 365 out from the proximal end 372. Removing the first filament 365 opens the third lumen 364—including a port to the second lumen 362 allowing removal of fluids from apertures 352. Similarly, when the third lumen 364 is blocked or a sufficient amount of time has passed, the second filament 399 may be removed from the fourth lumen 301 to provide flow through the fourth lumen 301.

Figure 11:
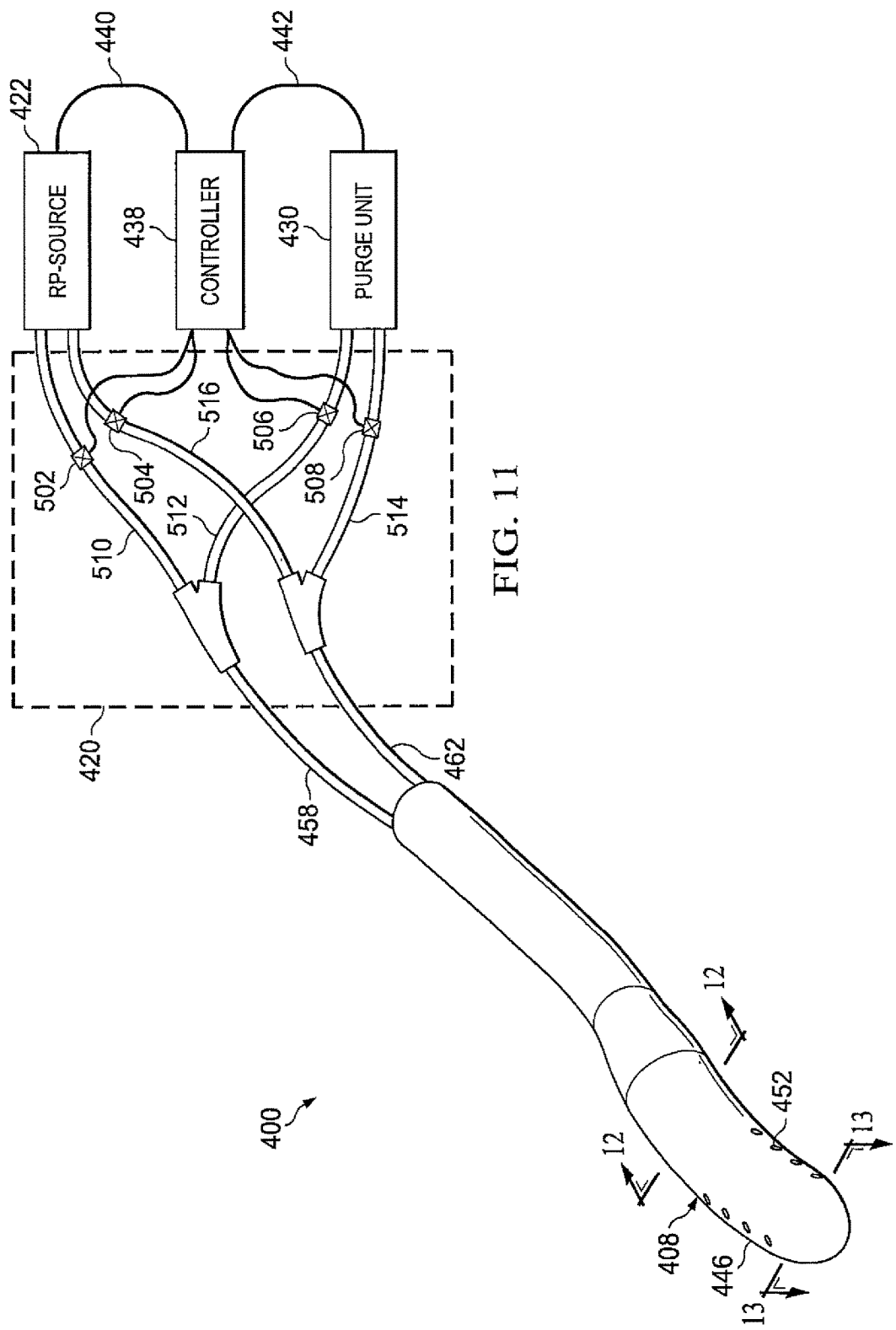
FIG. 11 is a schematic diagram, with a portion shown in perspective view, of an illustrative embodiment of a system for delivering reduced pressure to a subcutaneous tissue site.
Figure 12:
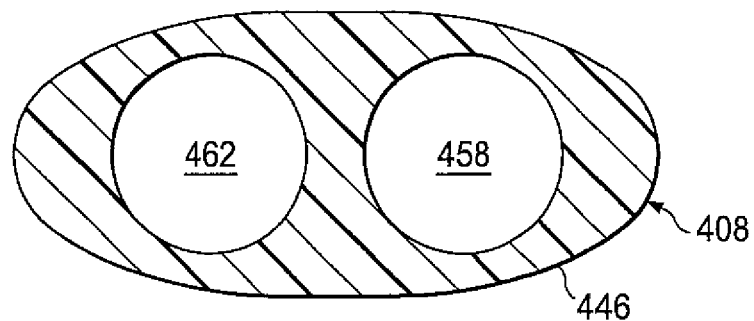
FIG. 12 is a schematic, lateral cross section of the multi-lumen applicator of FIG. 11 taken along line 12-12.
Figure 13:
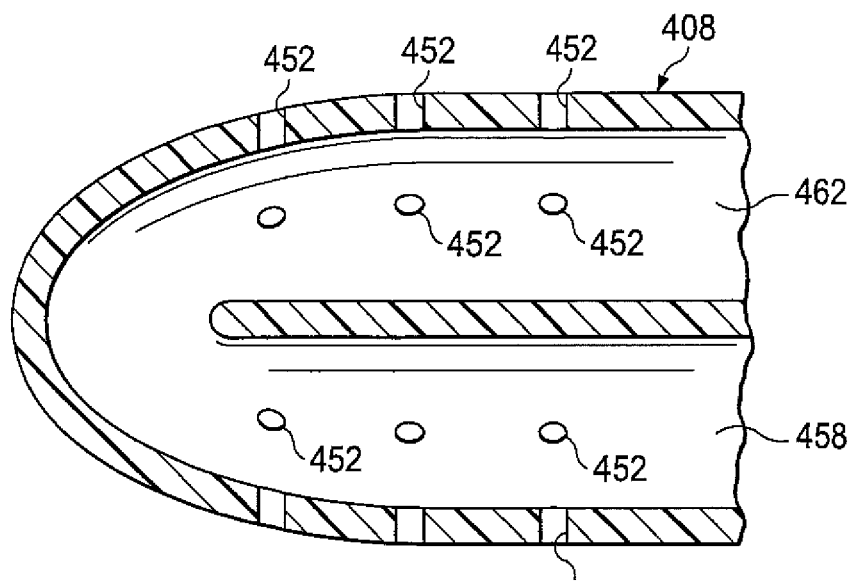
FIG. 13 is a longitudinal cross section taken in part along line 13-13 of the multi-lumen applicator of FIG. 11.

Referring now primarily to FIGS. 11-13, another illustrative embodiment of a system 400 for providing reduced pressure to a subcutaneous tissue site (and removing fluids therefrom) is presented. The system 400 includes a multi-lumen applicator 408. The multi-lumen applicator 408 is formed with an applicator body 446 that includes a plurality of apertures 452. The multi-lumen applicator 408 includes at least a first lumen 458 and a second lumen 462. The first lumen 458 may be selectively, fluidly coupled by a connector 420 to a reduced-pressure source 422 or a purge unit 430. The connector 420 is only one example of how the lumens 458, 462 may be reconfigured. Similarly, the second lumen 462 may be selectively, fluidly coupled to the purge unit 430 or the reduced-pressure source 422.

A controller 438 may be coupled by coupling lines 440, 442 to the reduced-pressure source 422 and the purge unit 430, respectively. The controller 438 may be coupled by additional coupling lines to a first valve 502, second valve 504, third valve 506, and fourth valve 508 in the connector 420. The controller 438 may control the reduced-pressure source 422, purge unit 430, and valves. The connector 420 may be under the control of the controller 438 and function to switch the functionality of the first lumen 458 and the second lumen 462.

After the first lumen 458 enters the connector 420 from the multi-lumen applicator 408, the lumen 458 may divide into a first sub-lumen 510 and a second sub-lumen 512. The first sub-lumen 510 couples the first lumen 458 to the reduced-pressure source 422. The first valve 502 is located on the first sub-lumen 510. The second sub-lumen 512 couples the first lumen 458 to the purge unit 430. The second sub-lumen 512 includes the third valve 506. In the initial state, the third valve 506 is closed and the first valve 502 is opened such that reduced pressure is supplied to the first lumen 458.

In a similar fashion, the second lumen 462 is divided within the connector 420 between a third sub-lumen 514 and a fourth sub-lumen 516. The third sub-lumen 514 fluidly couples the second lumen 462 to the purge unit 430. The fourth sub-lumen 516 fluidly couples the second lumen 462 to the reduced-pressure source 422. The fourth valve 508 is located on the third sub-lumen 514 and selectively controls fluid flow therein, and the second valve 504 is located in the fourth sub-lumen 516 and selectively controls flow therein.

In the initial state, the second lumen 462 serves as a purge lumen, and thus, the second valve 504 on the fourth sub-lumen 516 is closed and the fourth valve 508 is open on the third sub-lumen 514. When a blockage is determined by controller 438, a specified time has passed, or upon receiving manual instructions, the controller 438 will reconfigure the valves 502, 504, 506, 508 in order to reconfigure the functionality of the lumens 458, 462. Thus, for example, in a blockage condition or after the threshold time has elapsed, the first valve 502 on first sub-lumen 510 is closed and the third valve 506 on the second sub-lumen is opened. Additionally, the second valve 504 on the fourth sub-lumen 516 is opened and the fourth valve 508 on the third sub-lumen 514 is closed. Thus, in reconfigured position, the second lumen 462 becomes the evacuation lumen and the first lumen 458 becomes the purge lumen. This condition may be maintained or may only be temporarily assumed in order to remove the blockage in the first lumen 458.

Often reversing the flow for a period of time removes the blockage. Thus, it may be possible to return to the initial state and have the lumens function in that state again. Alternatively or in addition, an incompressible purging fluid, e.g., sterile saline, may be used in the retrograde direction of the first lumen 458 to remove the blockage. With respect to FIG. 11, reconfiguring the lumens 458, 462 may allow the blockage in the lumen to be removed more easily since the change causes flow in a retrograde direction. Once the blockage is removed, the original direction may be restored or operation may continue as configured. In addition, once the lumens 458, 462 are reconfigured to the second state, the pressure differentials and forces, which are limited in the ante grade direction, may be increased in the retro grade direction since greater pressure forces are more tolerable in the retrograde direction.

Figure 14:
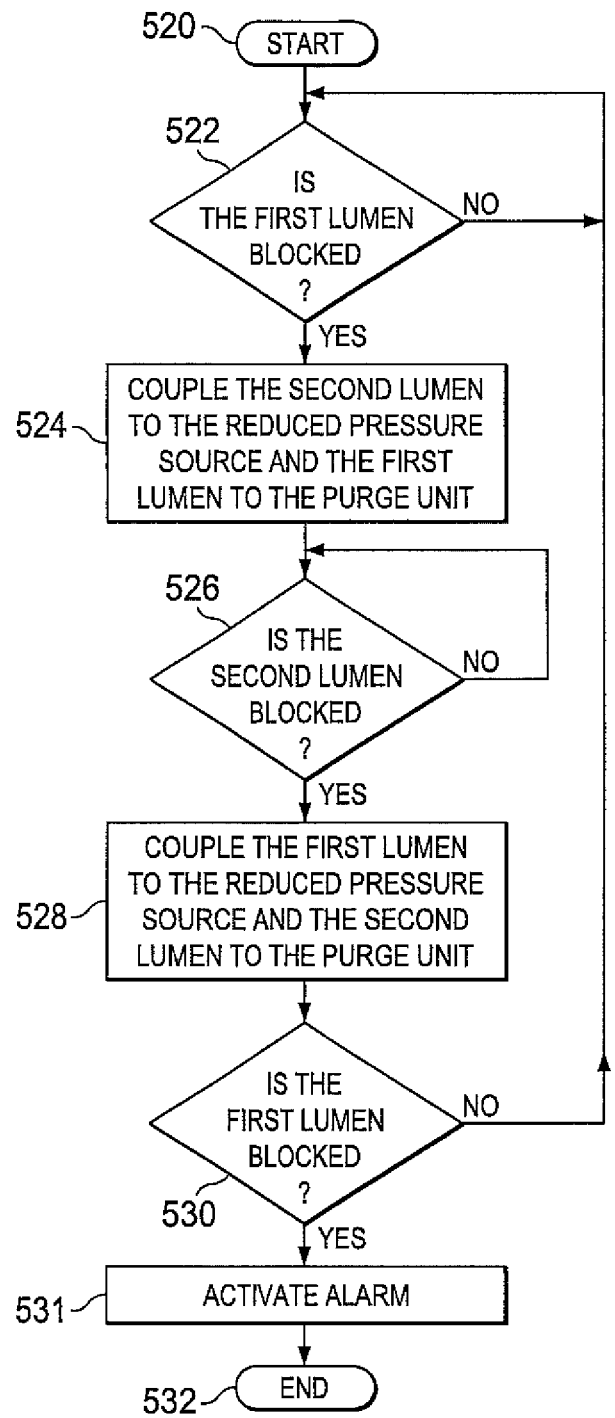
FIG. 14 is a schematic diagram showing an illustrative embodiment of a process for a controller used as part of a system for delivering reduced pressure to a subcutaneous tissue site.

Referring now to FIGS. 11 and 14 and primarily to FIG. 14, one illustrative, non-limiting logic flow for the controller 438 in controlling the functionality of the lumens 458, 462 is presented. The process begins at 520, with the first lumen in use for fluid evacuation, and goes to a first interrogation box 522 where the question is asked, "Is the first lumen blocked?" If the answered is in the negative, the process returns again to the first interrogation box 522. If the answer is in the affirmative, the process continues to process box 524 and instructions are provided for the second lumen 462 to be coupled to the reduced-pressure source 422 and the first lumen 458 to be coupled to the purge unit 430. This may be accomplished with the specific instructions sent to the valves, e.g., first valve 502 closed, second valve 504 open, third valve 506 open, and fourth valve 508 closed.

After resetting the valves 502, 504, 506, 508 to cause the reconfiguration of the lumens 458, 462, the next (second) interrogation box 526 is reached and the question is asked, "Is the second lumen blocked?" If the answer is in the negative, the process returns again to the second interrogation box 526. If in the affirmative, the process box 528 is reached. The process block 528 provides instructions for the first lumen 458 to be coupled to the reduced-pressure source 422 and the second lumen 462 to be coupled to the purge unit 430. In other words, the flow returns to the initial state which may now flow again since operation in the second state may remove blockages. After the process block 528, the third interrogation box 530 is reached and asks the question, "Is the first lumen blocked?" If the answer is negative, the process continues to the first interrogation box 522. If the answer to the third interrogation box 530 is in the affirmative, an alarm is activated at process block 531, and the process ends at step 532. This process is only one illustrative way of programming the controller 438.

In addition or in lieu of reconfiguring the flow of lumens, a blockage may be managed by removing the blockage. Referring now to FIGS. 15-19, a number of techniques for removing blockages from within the lumens in order to provide continued flow are presented. In these figures, a portion of a multi-lumen applicator 608 is presented. A plurality of apertures 652 are formed on the distal end 666 of an applicator body 646. A first lumen 658 is formed within the applicator body 646 as well as at least a second lumen 662. When a blockage exists, is suspected, or after set time period elapses, a blockage-removal device, e.g., a blockage-removal member 617, an elongated brush member 619, a fluid jet 621, or a purging element 623, is inserted into the multi-lumen applicator 608 and, the blockage-removal device is activated, which means the blockage-removal device may be removed, rotated, energized, or otherwise enabled to provide a blockage removing force within the lumen.

Figure 15:
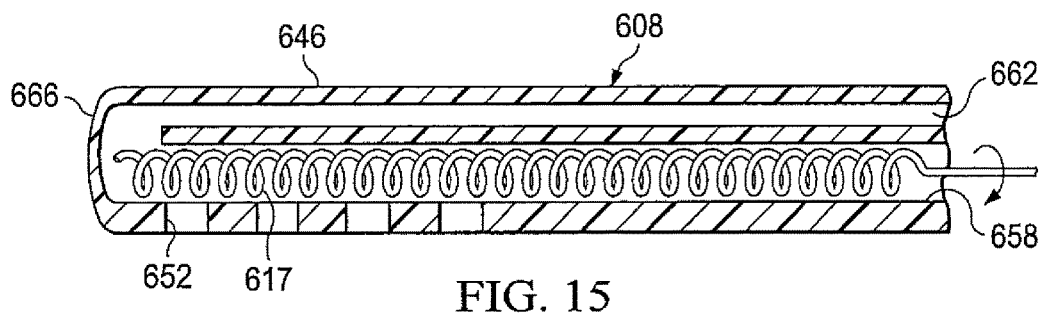
FIG. 15 is a schematic, longitudinal cross section of a distal portion of an illustrative embodiment of a multi-lumen applicator shown with a wire cleaning element.

Referring now primarily to FIG. 15, the blockage-removal member 617, such as an auger, Archimedes screw, or tanglement wire, is inserted into the first lumen 658 and rotated. For example, the blockage-removal member 617 may be rotated within the first lumen 658 to break a blockage free and help move any material with the flow toward the proximal end. The rotation may be at various speeds, e.g., slow rotation of 1 to 20 rpm. The blockage-removal member 617 remains within the first lumen 658 as the blockage-removal member 617 is rotated or may be slowly removed.

Figure 16:
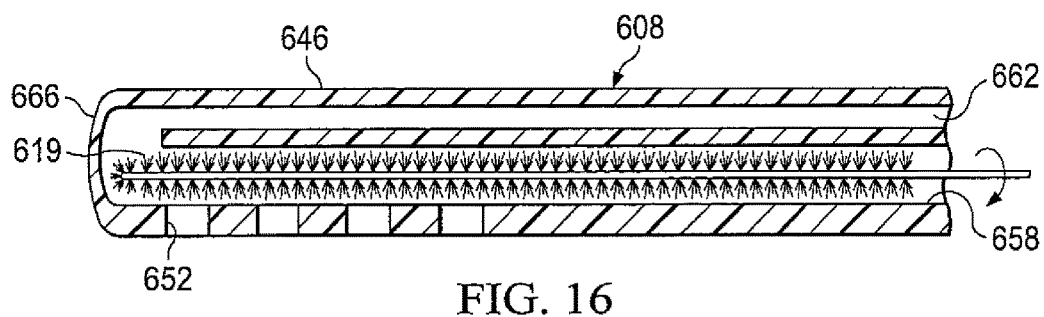
FIG. 16 is a schematic, longitudinal cross section of a distal portion of an illustrative embodiment of a multi-lumen applicator shown with a elongated brush.

Similarly, referring primarily to FIG. 16, the elongated brush member 619 disposed within the first lumen 658 is shown. The elongated brush member 619 may be rotated to remove items causing a block or inhibit flow. The elongated brush member 619 may be rotated at, for example, a relatively higher RPM.

Figure 17:
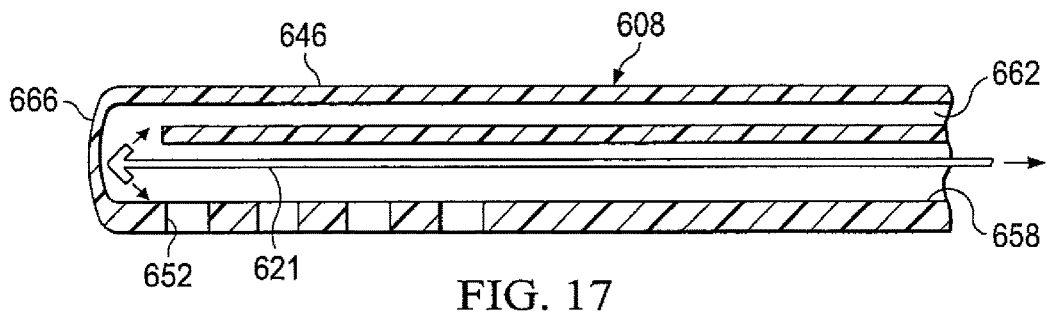
FIG. 17 is a schematic, longitudinal cross section of a distal portion of an illustrative embodiment of a multi-lumen applicator shown with a removable water jet.

Referring now primarily to FIG. 17, the fluid jet 621 is disposed within the first lumen 658 and removed from the first lumen 658 at the proximal end. As the fluid jet 621 is removed, water jets, which are facing the proximal end, remove any blockage. The volume of water or other purging liquid (e.g., saline) placed into the lumen will be matched with the evacuation capacity of the system in order to avoid fluid infusion into the patient.

Figure 18:
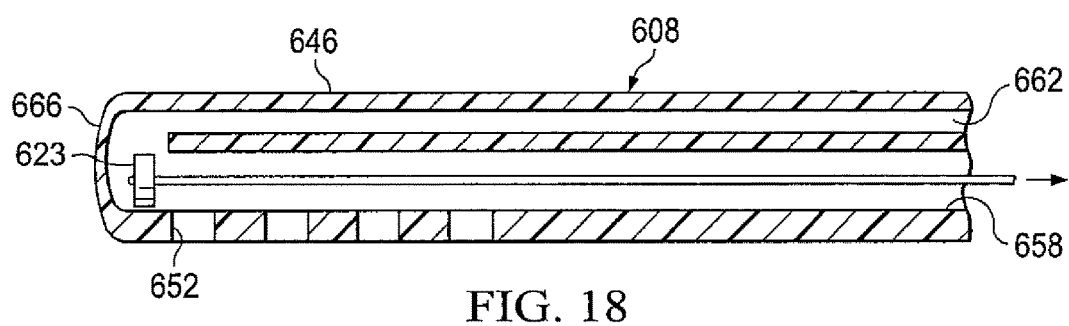
FIG. 18 is a schematic, longitudinal cross section of a distal portion of an illustrative embodiment of a multi-lumen applicator shown with a purging implement.
Figure 19:
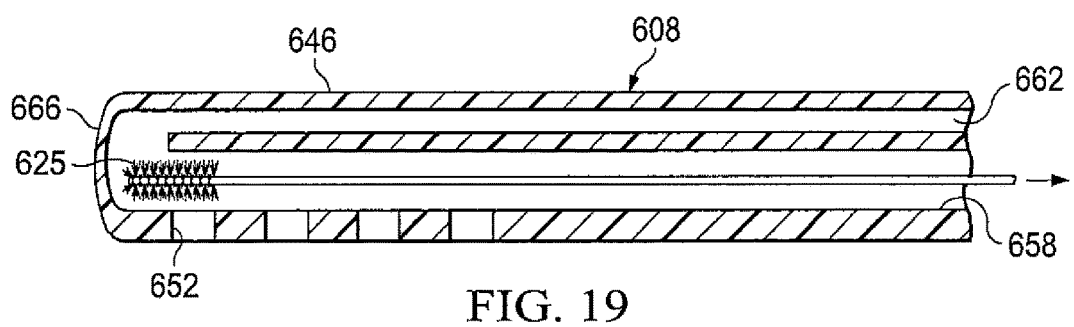
FIG. 19 is a schematic, longitudinal cross section of a distal portion of an illustrative embodiment of a multi-lumen applicator shown with a cytology brush.

Referring now primarily to FIG. 18, the purging element 623 may be pulled from a distal end of the first lumen 658 to a proximal end to remove any blockages in the first lumen 658. The purging element 623 or device 623 may be an inflatable member that after being located at the distal end may be inflated. For example, the purging element 623 may be analogous to a Fogerty catheter style device. Similarly, with reference primarily to FIG. 19, a cytology brush 625 may be pulled from the first lumen 658 to remove any blockages therein.

The embodiments of FIGS. 15-19 may optionally incorporate combined aspects of rotation and axial translation as part of the activation. The blockage-removal device may be in place when the applicator body 646 is placed into the wound. The blockage-removal device may be a single use item as it is removed from the applicator body 646.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

As will be appreciated, the various examples of ports opening at different times are given by way of example of the general principle that ports may be defined to open sequentially dependent on a range of parameters, including pressure or time. For example, ports may be defined to open at different pressures, or ports may be defined to dissolve after different lengths of exposure.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for providing reduced pressure to a tissue site and removing fluids from the tissue site, the system comprising:
    a multi-lumen applicator for distributing reduced pressure at the tissue site;
    a reduced-pressure source fluidly coupled to the multi-lumen applicator;
    a purging unit fluidly coupled to the multi-lumen applicator; and
    wherein the multi-lumen applicator comprises:
        an applicator body formed with a plurality of apertures,
        a first lumen initially fluidly configured to receive fluids from the tissue site through the plurality of apertures,
        a second lumen initially configured to provide a purging fluid to the first lumen, and
        a first frangible member disposed between the first lumen and second lumen, wherein the first frangible member is configured to rupture when exposed to a pressure differential greater than a first threshold pressure differential whereby at least a portion of the second lumen and a portion of the first lumen become fluidly coupled.

2. The system of claim 1, wherein the multi-lumen applicator further comprises:
    a second frangible member operable to rupture when exposed to a pressure differential greater than a second threshold pressure differential; and
    a third lumen fluidly coupled to the plurality of apertures but for the second frangible member, whereby when the second frangible member ruptures, the third lumen is fluidly coupled to the plurality of apertures.

3. A system for treating a tissue site, comprising:
    a multi-lumen applicator for distributing reduced pressure at the tissue site;
    a reduced-pressure source fluidly coupled to the multi-lumen applicator;
    a purging unit fluidly coupled to the multi-lumen applicator; and
    wherein the multi-lumen applicator comprises:
        an applicator body formed with a plurality of apertures,
        a first lumen initially fluidly configured to receive fluids from the tissue site through the plurality of apertures,
        a second lumen initially configured to provide a purging fluid to the first lumen, and
        an activation member disposed between the first lumen and second lumen, wherein the activation member is configured to fluidly couple, when activated, at least a portion of the second lumen and a portion of the first lumen whereby at least a portion of the second lumen transports the fluids from the tissue site over at least a portion of the second lumen.

4. The system of claim 3, wherein the first activation member comprises a first frangible member that is activated when exposed to a pressure differential greater than a first threshold pressure differential.

5. The system of claim 3, wherein the first activation member comprises a first frangible member that is activated when exposed to a fluid.

6. The system of claim 3, wherein the first activation member comprises a first frangible member that is activated when exposed to a liquid.

7. The system of claim 3, wherein the first activation member comprises a pressure-activated valve.

8. The system of claim 3, wherein the multi-lumen applicator further comprises:
    a third lumen initially configured to provide a purging fluid to the first lumen, and
    a second activation member disposed between the third lumen and the first lumen, wherein the second activation member is configured, when activated, to fluidly couple at least a portion of the third lumen to at least a portion the first lumen to transport the fluids from the tissue site over at least a portion of the third lumen.

9. A multi-lumen applicator for treating a tissue site, comprising:
    an applicator body having a distal end and a proximal end and formed with a plurality of apertures proximate the distal end for receiving fluid and for delivering reduced pressure;
    a first lumen fluidly coupled to the plurality of apertures;
    a first activation member having at least a closed position and an open position, the first activation member comprising a first frangible member that ruptures when activated; and
    a second lumen fluidly coupled to the plurality of apertures when the first activation member is in the open position but not when the first activation member is in the closed position, whereby when the first activation member is moved to the open position, the second lumen is fluidly coupled to the plurality of apertures.

10. The multi-lumen applicator of claim 9, wherein the first frangible member is activated when a pressure differential at the first frangible member exceeds a first threshold pressure differential.

11. The multi-lumen applicator of claim 9, wherein the first frangible member is activated when exposed to liquid for greater than a threshold time.

12. A method for providing reduced pressure to a tissue site, the method comprising:
   providing a multi-lumen applicator for distributing reduced pressure at the tissue site;
   wherein the multi-lumen applicator comprises:
      an applicator body formed with a plurality of apertures, a purge lumen, and a first lumen fluidly coupled to the plurality of apertures and to the purge lumen,
      an activation member operable to move from a closed position to an open position when activated, and
      a second lumen formed in the applicator body and fluidly coupled to the purge lumen when the activation member is in the open position;
   disposing the multi-lumen applicator proximate to the tissue site;
   removing fluids from the tissue site through the first lumen;
   activating the activation member of the multi-lumen applicator such that the second lumen is fluidly coupled to the purge lumen; and
   removing fluids from the tissue site at least partially through the second lumen after activating the activation member.

13. The method of claim 12, wherein the activation member comprises a frangible member that ruptures when exposed to a pressure differential greater than a first threshold pressure differential.

14. The method of claim 12, wherein the activation member comprises a frangible member that ruptures when exposed to a fluid.

15. The method of claim 12, wherein the activation member comprises a frangible member that ruptures when exposed to a liquid.

* * * * *